United States Patent
Machhammer et al.

(10) Patent No.: US 6,388,129 B1
(45) Date of Patent: May 14, 2002

(54) METHOD FOR PRODUCING ACROLEIN AND/OR ACRYLIC ACID FROM PROPANE

(75) Inventors: Otto Machhammer, Mannheim; Andreas Tenten, Maikammer; Harald Jachow, Bensheim; Susanne Haupt, Offenbach; Heiko Arnold; Signe Unverricht, both of Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/763,223
(22) PCT Filed: Aug. 10, 1999
(86) PCT No.: PCT/EP99/05791
§ 371 Date: Feb. 20, 2001
§ 102(e) Date: Feb. 20, 2001
(87) PCT Pub. No.: WO00/10960
PCT Pub. Date: Mar. 2, 2000

(30) Foreign Application Priority Data

Aug. 19, 1998 (DE) .......................................... 198 37 518

(51) Int. Cl.$^7$ .......................... C07C 51/16; C07C 51/42
(52) U.S. Cl. ........................ 562/545; 562/545; 562/600
(58) Field of Search ................................. 562/545, 600

(56) References Cited

U.S. PATENT DOCUMENTS

| | | | |
|---|---|---|---|
| 3,161,670 A | 12/1964 | Adams et al. | |
| 3,798,283 A | 3/1974 | Bitar et al. | |
| 4,066,704 A | 1/1978 | Harris et al. | |
| 4,532,365 A | * 7/1985 | Khoobiar et al. | |
| 5,183,936 A | 2/1993 | Etzkorn et al. | |
| 5,198,578 A | 3/1993 | Etzkorn et al. | |

FOREIGN PATENT DOCUMENTS

| | | |
|---|---|---|
| CA | 110 5352 | 7/1995 |
| EP | 0 117 446 | 9/1984 |
| EP | 0 293 224 | 11/1988 |
| WO | WO 97/36849 | 10/1997 |
| WO | WO-97/36849 | * 10/1997 |

OTHER PUBLICATIONS

Young–Chul Kim et al, Applied Catalysis, 70, 1991 , 175–187.*
Pavia et al, Organic Laboratory Techniques, Saunders College Publishing, second edition, p. 693.*
Y–C. Kim, et al., Applied Catalysis, vol. 70, No. 2, pp. 175–187, "Selective Oxidation of Propane Involving Homogeneous and Heterogeneous Steps Over Multicomponent Metal Oxide Catalysts", 1991.
Y–C. Kim, et al., Catalysis Today, vol. 13, No. 4, pp. 673–678, "Catalytic (amm) Oxidation of Propane with Molecular Oxygen Over Complex Metal Oxides: Involvement of Homogeneous Reaction in Gas Phase", 1992.

* cited by examiner

Primary Examiner—Paul J. Killos
Assistant Examiner—Farhad Forohar
(74) Attorney, Agent, or Firm—Oblon, Spivak, McClelland, Maier & Neustadt, P.C.

(57) ABSTRACT

In a process for the preparation of acrolein and/or acrylic acid from propane, the propane is subjected, in a first reaction stage, to a partial oxydehydrogenation with molecular oxygen under homogeneous and/or heterogeneous catalysis to give propene and the product gas mixture formed in the first reaction stage is then used for the preparation of acrolein and/or acrylic acid by gas-phase catalytic propene oxidation.

7 Claims, 2 Drawing Sheets

METHOD FOR PRODUCING ACROLEIN AND/OR ACRYLIC ACID FROM PROPANE

BACKGROUND OF THE INVENTION

FIELD OF THE INVENTION

The present invention relates to a process for the preparation of acrolein and or acrylic acid from propane, in which the propane is subjected, in a first reaction stage, to a partial oxydehydrogenation with molecular oxygen under homogeneous and/or heterogenous catalysis to give propene and the propene-containing product gas mixture formed in the first reaction stage is then used in at least one further reaction stage for the preparation of acrolein and/or acrylic acid by gas-phase catalytic propene oxidation.

DESCRIPTION OF THE INVENTION

Acrolein and acrylic acid are important intermediates which are used, for example, in the preparation of active ingredients and polymers.

The process predominantly used at present on an industrial scale for the production of acrolein and/or acrylic acid is the gas-phase catalytic oxidation of propene (e.g. EP-A 575 897), the propene being produced predominantly as a byproduct of ethylene production by steam cracking of naphtha.

Since the other fields of use of propene, for example the preparation of polypropylene, are constantly expanding it would be advantageous to have an industrially usable, competitive process for the preparation of acrolein and/or acrylic acid, whose raw material base is not propene but, for example, the propane naturally occurring in large quantities as a natural gas component.

U.S. Pat. No. 3,798,283 discloses that propane can be oxydehydrogenated homogeneously to propene in the presence of molecular oxygen at elevated temperatures. Suitable oxygen sources are both pure oxygen and mixtures of oxygen and inert gas.

DE-A 20 58 054 and DE-A 1 95 30 454 disclosed that the oxydehydrogenation of propane to propene can also be carried out under heterogeneous catalysis.

U.S. Pat. No. 3,161,670, EP-A 117 446 and DE-A 33 13 573 relate to processes for the preparation of acrolein and/or acrylic acid, in which propane is first dehydrogenated under heterogeneous catalysis in the absence of oxygen to give propene.

The propene-containing product mixture is then subjected to a gas-phase oxidation under heterogeneous catalysis. However, the disadvantage of this procedure is that the catalyst required for the nonoxidative dehydrogenation of the propane is relatively rapidly deactivated by carbon deposits and therefore has to be regenerated frequently. A further disadvantage of this procedure is the hydrogen formation associated with the nonoxidative propane dehydrogenation.

It is true that DE-A 33 13 573 mentions the basic possibility of coupling oxidative dehydrogenation of propane to propene with subsequent propene oxidation under heterogeneous catalysis. However, it does not contain more detailed information on carrying out such a process.

EP-A 293 224, U.S. Pat. Nos. 5,198,578 and 5,183,936 state that a high proportion of $N_2$ in the diluent gas of the catalytic gas-phase oxidation of propene to acrolein and/or acrylic acid is disadvantageous. EP-A 293 224 furthermore suggests combining the oxidative dehydrogenation of propane to propene and the catalytic gas-phase oxidation of propene for the preparation of acrolein and/or acrylic acid with one another.

In Catalysis Today 13, (1992), 673 to 678, Moro-oka et al. combine a homogenous oxidative dehydrogenation of propane to propene with a subsequent oxidation of the dehydrogenation product mixture under heterogeneous catalysis to give acrolein and/or acrylic acid in laboratory experiments. The corresponding combination of processes is recommended by Moro-oka et al. in Applied Catalysis, 70 (2), (1991), 175 to 187. In accordance with the recommendation of EP-A 293 224, of U.S. Pat. No. 5,198,578 and of U.S. Pat. No. 5,183,936, Moro-oka et al. use either pure molecular oxygen or air enriched with oxygen as the oxygen source for the oxydehydrogenation stage in all cases. For the latter case, Moro-oka suggests no separation at all, in the further course of his process, of nitrogen introduced into the process.

CN-A 110 5352 likewise discloses a homogenous oxidative dehydrogenation of propane to propene with a subsequent oxidation of the dehydrogenation product mixture under heterogeneous catalysis to give acrolein and/or acrylic acid. Since CN-A 110 5352 relates to a procedure to be carried out on industrial scale, CN-A 110 5352, following the recommendation of EP-A 293 45 224, of U.S. Pat. No. 5,198,578 and of U.S. Pat. No. 5,183,936, uses exclusively pure molecular oxygen as the oxygen source.

WO 97/36849 relates to the combination of a catalytic oxidative dehydrogenation of propane to propene with a subsequent oxidation of the dehydrogenation product mixture under heterogeneous catalysis to give acrolein and/or acrylic acid in an industrial embodiment.

Although WO 97/36849 does not rule out the use of nitrogen-containing oxygen (e.g. air) as a source of the molecular oxygen required for the oxydehydrogenation, it advises against such a use. Moreover, for a continuous procedure with recycled gas for suppressing an undesired concentration of disadvantageous components of the reaction gas mixture, WO 97/36849 suggests merely a purge of recycled gas and no separation of components from the recycled gas.

For cost-efficiency reasons, essentially only air is suitable as a starting material for the molecular oxygen source for industrial gas-phase oxidation.

Against this background, the abovementioned procedures are disadvantageous in that, owing to the similarity of $O_2$ and $N_2$, the sole measure of a prior nitrogen/oxygen separation, starting from air, for the preparation of pure oxygen or of an air depleted in nitrogen for limiting the nitrogen content in a subsequent oxidation of the propene contained in the dehydrogenation product mixture is very energy-consumptive.

SUMMARY OF THE INVENTION

It is an object of the present invention to provide a process for the preparation of acrolein and/or acrylic acid from propane, in which the propane is subjected, in a first reaction stage, to an oxydehydrogenation with molecular oxygen under homogeneous and/or heterogeneous catalysis to give propene and the propene-containing product gas mixture formed in the first reaction stage is then used in at least one further reaction stage for the preparation of acrolein and/or acrylic acid by gas-phase catalytic propene oxidation, and in which the nitrogen content in the propene oxidation stage is limited in a less energy-consumptive manner than in the prior art.

DETAILED DESCRIPTION OF THE INVENTION

We have found this object is achieved by a process for the preparation of acrolein and/or acrylic acid from propane, in which the propane is subjected, in a first reaction stage, to a partial oxydehydrogenation with molecular oxygen under homogeneous and/or heterogeneous catalysis to give propene and the propene-containing product gas mixture formed in the first reaction stage is then used in at least one further reaction stage for the preparation of acrolein and/or acrylic acid by gas-phase catalytic propene oxidation, wherein the molecular oxygen required in the first reaction stage and differing from recycled oxygen gas is added as nitrogen-containing modified air to the reaction gas starting mixture of the first reaction stage, with the proviso that the nitrogen content (expressed in mol %) of the modified air is less than, and the oxygen content of the modified air is greater than, the corresponding contents of air (i.e. air depleted in nitrogen), and wherein at least a part of the molecular nitrogen contained in the product gas mixture is separated from said mixture before the further use of propene-containing product gas mixture, formed in the first reaction stage, for the preparation of acrolein and/or acrylic acid in the at least one further reaction stage.

Detailed research shows that the basic advantageousness of the novel procedure over the most closely related prior art process is due to the fact that the chemical bonding of the molecular oxygen which takes place in the oxidative dehydrogenation of propane with the use of a nitrogen-containing oxygen source implicitely performs part of the separation work to be performed for separating atmospheric nitrogen and atmospheric oxygen. The difference between the resulting, oxygen-containing, polar compounds (e.g. $H_2O$) and $N_2$ is substantially more pronounced than the difference between $N_2$ and $O_2$, which is why a partial or complete subsequent $N_2$ separation from the product mixture of the oxidative dehydrogenation is substantially less energy-consumptive than a separation of $N_2$ from air which is carried out exclusively beforehand.

If, in the novel process, the first reaction stage is designed as a homogeneous oxydehydrogenation, this can in principle be carried out, for example, as described in U.S. Pat. No. 3,798,283, CN-A 1 105 352, Applied Catalysis, 70 (2), (1991), 175 to 187, Catalysis Today 13, (1992), 673 to 678 and the prior application DE-A 1 96 22 331, except that, according to the invention, modified air should be used as the oxygen source (apart from recycle oxygen gas).

The temperature of the homogeneous oxydehydrogenation is expediently chosen to be from 300 to 700° C., preferably from 400 to 600° C., particularly preferably from 400 to 500° C. The operating pressure may be from 0.5 to 100 bar or from 1 to 50 bar. It is frequently from 1 to 20 bar or from 1 to 10 bar.

The residence time of the reaction gas mixture under oxydehydrogenation conditions is usually from 0.1 or 0.5 to 20, preferably from 0.1 or 0.5 to 5, seconds. The reactor used may be, for example, a tube furnace or a tube-bundle reactor, for example a countercurrent tube furnace with stack gas as a heating medium, or a tube-bundle reactor with salt melt as a heating medium.

The propane to oxygen ratio in the reaction gas starting mixture to be used may be from 0.5:1 to 40:1. According to the invention, it is advantageous that the molar ratio of propane to molecular oxygen in the reaction gas starting mixture is $\leq 6:1$ or $\leq 5:1$. As a rule, the abovementioned ratio is $\leq 1:1$ or $\leq 2:1$. The nitrogen content of the reaction gas starting mixture is as a rule a consequence of the abovementioned requirement since the reaction gas starting mixture usually comprises essentially no further gases apart from propane and modified air. Of course, the reaction gas starting mixture can however also comprise further, essentially inert components, such as $H_2O$, $CO_2$, CO, noble gases and/or propene. Propene is a component of the reaction gas starting mixture, for example, when the starting propane used is the $C_3$ fraction from the refinery or the $C_3$ fraction from the light hydrocarbons from the oilfield, which may have a propene content of up to 10% by weight. Furthermore, it is a component of said mixture when the novel process is carried out continuously and, after the last reaction step, unconverted propane and/or propene are recycled to the oxydehydrogenation. Components recycled to the oxydehydrogenation are referred to in this publication very generally as recycled gas. Owing to the gas recycling, the nitrogen content of the reaction gas starting mixture may be up to 60 mol % or up to 50 mol %. Gas recycling may also lead to the reaction gas starting mixture containing up to 5 mol % of gases such as CO, $CO_2$, ethene and $H_2O$ in the continuous procedure. It is advantageous for a homogeneous oxidative dehydrogenation of propane to propene if the ratio of the surface area of the reaction space to the volume of the reaction space is very low. This is a consequnce of the free radical mechanism of the homogeneous oxidative propane dehydrogenation since reaction space surfaces generally act as free radical acceptors. Particularly advantageous surface materials are aluminas, quartz glass, borosilicates, stainless steel and aluminum.

If, in the novel process, the first reaction stage is designed as an oxydehydrogenation under heterogeneous catalysis, this can in principle be carried out, for example, as described in U.S. Pat. No. 4,788,371, CN-A 10 733 893, Catalysis Letters 23 (1994) 103–106, W. Zhang, Gaodeng Xuexiao Huaxue Xuebao, 14 (1993) 566, Z. Huang, Shiyou Huagong, 21 (1992) 592, WO 97/36849, DE-A 1 97 53 817, U.S. Pat. Nos. 3,862,256, 3,887,631, DE-A 1 95 30 454, U.S. Pat. No. 4,341,664, J. of Catalysis 167, (1997), 560–569, J. of Catalysis 167, (1997), 550–559, Topics in Catalysis 3 (1996), 265–275, U.S. Pat. No. 5,086,032, Catalysis Letters 10 (1991), 181–192, Ind. Eng. Chem. Res. 35 (1996), 14–18, U.S. Pat. No. 4,255,284, Applied Catalysis A: General, 100 (1993), 111–130, J. of Catalysis 148 (1994), 56–67, V. Cortés Corberán and S. Vic Bellón (Editors), New Developments in Selective Oxidation II, 1994, Elsevier Science B. V., pages 305–313, 3rd World Congress on Oxidation Catalysis, R. K. Grasselli, S. T. Oyama, A. M. Gaffney and J. E. Lyons (Editors), 1997, Elsevier Science B. V., page 375 et seq., except that, according to the invention, modified air should be used as the oxygen source (apart from recycle oxygen gas). In particular, all oxydehydrogenation catalysts stated in the abovementioned publications may be used. The statements made in connection with the abovementioned publications are also applicable to:

a) Otsuka, K.; Uragami, Y.; Komatsu, T.; Hatano, M. in Natural Gas Conversion, Stud. Surf. Sci. Catal.; Holmen A.; Jens, K.-J.; Kolboe, S., Eds.; Elsevier Science: Amsterdam, 1991; Vol. 61, p 15;

b) Seshan, K.; Swaan, H. M.; Smits, R. H. H.; van Ommen, J. G.; Ross, J. R. H. in New Developments in Selective Oxidation; Stud. Surf. Sci. Catal.; Centi, G.; Trifirb, F., Eds.; Elsevier Science: Amsterdam 1990; Vol. 55, p 505;

c) Smits, R. H. H.; Seshan, K.; Ross, J. R. H. in New Developments in Selective Oxidation by Heterogeneous Catalysis; Stud. Surf. Sci. Catal.; Ruiz, P.; Delmon, B., Eds.; Elsevier Science: Amsterdam, 1992 a; Vol. 72, p 221;

d) Smits, R. H. H.; Seshan, K.; Ross, J. R. H. Proceedings, Symposium on Catalytic Selective Oxidation, Washington D. C.; American Chemical Society: Washington, D. C., 1992 b; 1121;

e) Mazzocchia, C.; Aboumrad, C.; Daigne, C.; Tempesti, E.; Herrmann, J. M.; Thomas, G. Catal. Lett. 10 (1991), 181;

f) Bellusi, G.; Conti, G.; Perathonar, S.; Trifirò, F. Proceedings, Symposium on Catalytic Selective Oxidation, Washington, D. C.; American Chemical Society: Washington, D. C., 1992; p 1242;

g) Ind. Eng. Chem. Res. 35 (1996), 2137–2143 and h) Symposium on Heterogeneous Hydrocarbon Oxidation Presented before the Division of Petroleum Chemistry, Inc. 211th National Meeting, American Chemical Society New Orleans, La., Mar. 24–29, 1996.

Oxydehydrogenation catalysts particularly suitable according to the invention are the multimetal oxide materials or multimetal oxide catalysts A of DE-A 1 97 53 817, the multimetal oxide materials or multimetal oxide catalysts A stated as being preferred in the abovementioned publication being very particularly advantageous, i.e. particularly suitable active materials are multimetal oxide materials of the formula I $$M^1_a Mo_{1-b} M^2_b O_x \quad (I),$$

where $M^1$ is Co, Ni, Mg, Zn, Mn and/or Cu, $M^2$ is W, V, Te, Nb, P, Cr, Fe, Sb, Ce, Sn and/or La, a is from 0.5 to 1.5, b is from 0 to 0.5 and x is a number which is determined by the valency and frequency of the elements in I other than oxygen.

In principle, active materials I suitable according to the invention can be prepared in a simple manner by producing, from suitable sources of their elemental constituents, a very intimate, preferably finely divided dry blend having a composition corresponding to their stoichiometry and calcining said dry blend at from 450 to 1000° C. The calcination can be carried out both under inert gas and under an oxidizing atmosphere, e.g. air (mixture of inert gas and oxygen) and also under a reducing atmosphere (e.g. mixture of inert gas, oxygen and $NH_3$, CO and/or $H_2$). The duration of calcination may be from a few minutes to a few hours and usually decreases with the temperature. Suitable sources of the elemental constituents of the multimetal oxide active materials I are those compounds which are already oxides and/or those compounds which can be converted into oxides by heating, at least in the presence of oxygen.

In addition to the oxides, suitable starting compounds of this type are in particular halides, nitrates, formates, oxalates, citrates, acetates, carbonates, amine complex salts, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and or ammonium oxalate, which, at the latest during the subsequent calcination, decompose and/or can be decomposed into compounds escaping completely in gaseous form may additionally be incorporated into the intimate dry blend). The intimate mixing of the starting compounds for the preparation of multimetal oxide materials I can be carried out in dry or in wet form. If it is effected in dry form, the starting compounds are expediently used in the form of finely divided powders and, after mixing and, if required, compaction, are subjected to the calcination. Preferably, however, the intimate mixing is effected in wet form. Usually, the starting compounds are mixed with one another in the form of an aqueous solution and/or suspension. In the dry process described, particularly intimate dry blends are obtained when exclusively dissolved sources of the elemental constituents are used as starting materials. Water is preferably used as the solvent. The aqueous material obtained is then dried, the drying process preferably being effected by spray-drying the aqueous mixture with outlet temperatures of from 100 to 150° C. Particularly suitable starting compounds of Mo, V, W and Nb are their oxo compounds (molybdates, vanadates, tungstates and niobates) or the acids derived from these. This applies in particular to the corresponding ammonium compounds (ammonium molybdate, ammonium vanadate, ammonium tungstate).

The multimetal oxide materials I can be used for the novel process both in powder form and after shaping to specific catalyst geometries, where the shaping may be effected before or after the final calcination. For example, unsupported catalysts can be prepared from the powder form of the active material or its uncalcined precursor material by compaction to the desired catalyst geometry (for example by pelleting or extrusion), it being possible, if required, to add assistants, for example graphite or stearic acid as lubricant, and/or molding assistants and reinforcing materials, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinders, a wall thickness of from 1 to 3 mm is expedient. Suitable hollow cylinder geometries are, for example, 7 mm×7 mm×4 mm or 5 mm×3 mm×2 mm or 5 mm×2 mm×2 mm (in each case length×external diameter× internal diameter). Of course, the unsupported catalyst may also have spherical geometry, where the sphere diameter may be from 2 to 10 mm.

The shaping of the pulverulent active material or of its pulverulent, still uncalcined precursor material can of course also be carried out by application to preshaped inert catalyst supports. The coating of the supports for the preparation of the coated catalysts is effected as a rule in a suitable rotatable container, as diclosed, for example, in DE-A 2909671 or EP-A 10 293859. Expediently, for coating the supports, the powder material to be applied can be moistened and, after application, can be dried again, for example by means of hot air. The coat thickness of the powder material applied to the support is expediently chosen in the range from 50 to 500 μm, preferably from 150 to 250 μm.

The support materials used may be conventional porous or nonporous aluminas, silicon dioxide, thorium dioxide, zirconium dioxide, silicon carbide or silicates, such as magnesium silicate or aluminum silicate. The supports may have a regular or an irregular shape, those having a regular shape with pronounced surface roughness, for example spheres or hollow cylinders, being preferred. The use of essentially nonporous, spherical steatite supports which have a rough surface and whose diameter is from 1 to 8 mm, preferably from 4 to 5 mm, is suitable.

The reaction temperature of the oxydehydrogenation of the propane under heterogeneous catalysis is expediently chosen in the range from 300 to 600° C., frequently from 350 to 500° C. The recommended operating pressure is from 0.5 to 10 bar or from 1 to 10 bar or from 1 to 5 bar. Operating pressures above 1 bar, for example from 1.5 to 10 bar, have proven advantageous. As a rule, the oxydehydrogenation of the propane under heterogeneous catalysis is carried out over a fixed catalyst bed. The latter is expediently poured into the tubes of a tube-bundle reactor, as described, for example, in EP-A 700 893 and EP-A 700 714 and in the literature cited in these publications. The average residence time of the reaction gas mixture in the catalyst bed is usually from 0.5 to 20 seconds. The propane to oxygen ratio in the reaction gas starting mixture to be used for the propane oxydehydrogenation under heterogeneous catalysis may be, according to the invention, from 0.5:1 to 40:1. It is advantageous according to the invention if the molar ratio of propane to molecular oxygen in the reaction gas starting mixture is $\leq 6:1$ or $\leq 5:1$. As a rule, the abovementioned ratio is $\leq 1:1$ or 2:1. The nitrogen content of the reaction gas starting mixture is as a rule a consequence of the abovementioned requirement since said mixture usually comprises essentially no further gases apart from propane and modified air. However, the reaction gas starting mixture can of course also comprise further, essentially inert components, such as $H_2O$, $CO_2$, CO, noble gases and/or propene. Propene is a component of the reaction gas starting mixture, for example, when the starting propene used is the $C_3$ fraction from the refinery or the $C_3$ fraction from the light hydrocarbons from the oilfield, which may have a propene content of up to 10% by weight. Furthermore, it is a component of the said mixture when the novel process is carried out continuously and, after the last reaction step, unconverted propane and/or propene are recycled to the oxydehydrogenation under heterogeneous catalysis. Owing to the gas recycling, the nitrogen content of the reaction gas starting mixture of the propane oxydehydrogenation under heterogeneous catalysis in the novel process may be up to 60 mol % or up to 50 mol % in the case of the continuous procedure. Gas recycling may also lead to the reaction gas starting mixture in the case of a continuous procedure containing up to 5 mol % of gases such as CO, $CO_2$, ethane, methane, ethene and/or $H_2O$. The modified air to be used according to the invention as the oxygen source may contain, for example, from $\geq 0.05$ to <78% by volume or from $\geq 0.1$ to $\leq 75\%$ by volume of $N_2$, i.e. the nitrogen content of the modified air to be used according to the invention as the oxygen source may be from $\geq 1$ to $\leq 70\%$ by volume or from $\geq 5$ to $\leq 60\%$ by volume or from $\geq 10$ to $\leq 50\%$ by volume or from $\geq 15$ to $\leq 40\%$ by volume or from $\geq 20$ to $\leq 30\%$ by volume.

Accordingly, the oxygen content of modified air to be used according to the invention as the oxygen source may be from >20.95 to 99.95% by volume or from $\geq 25$ to $\leq 99.9\%$ by volume or from $\geq 30$ to $\leq 99\%$ by volume or from $\geq 40$ to $\leq 95\%$ by volume or from $\geq 50$ to $\leq 90\%$ by volume or from $\geq 60$ to $\leq 85\%$ by volume or from $\geq 70$ to $\leq 80\%$ by volume.

In addition to oxygen and nitrogen, the modified air to be used according to the invention may also contain the other components usually present in small amounts in air, such as noble gases, carbon dioxide, water vapor, etc. However, the abovementioned components may of course also have been partially or completely separated off in the modification.

The modified air to be used according to the invention as the oxygen source can be produced in a very simple manner, for example by fractional distillation of air, preferably under pressure. It is of course also possible to use the processes of EP-A 848 981 and EP-A 848639.

Expediently, the $O_2$ conversion of the homogeneous and the catalytic oxidative propane dehydrogenation in the novel process (with a single pass) should be $\geq 70$ mol %, i.e. the abovementioned $O_2$ conversion may be $\geq 75$ mol % or $\geq 80$ mol % or $\geq 85$ mol % or $\geq 90$ mol % or $\geq 95$ mol % or $\geq 97$ mol % or $\geq 99$ mol %.

According to the invention, homogeneous and catalytic propane oxydehydrogenation can of course also be used in combination.

The product gas mixture of the propane oxydehydrogenation may contain, for example, the following components as possible components: $CO_2$, CO, $H_2O$, $N_2$, $O_2$, propene, propane, ethane, ethene, methane, acrolein, acrylic acid, ethylene oxide, butane, acetic acid, formaldehyde, formic acid, propylene oxide and butene.

The removal of at least a part of the nitrogen contained in the propane oxydehydrogenation product gas mixture, which is required according to the invention before the further use of the abovementioned, propene-containing propane oxydehydrogenation product gas mixture for the preparation of acrolein and/or acrylic acid from said mixture, can be carried out, for example, in a simple manner by distillation.

Fractional distillation is expediently used, preferably fractional distillation under pressure at low temperatures. The pressure to be used may be, for example, from 10 to 100 bar. Packed columns or tray columns may be used as rectification columns. Suitable tray columns are those having dual-flow trays, bubble trays or valve trays. The reflux ratio may be, for example, from 1 to 10. Other possibilities for nitrogen removal are, for example, pressure swing absorption, scrubbing under pressure and extraction under pressure.

The amount of nitrogen to be separated off according to the invention may be 5% or 10% or 20% or 30% or 40% or 50% or 60% or 70% or 80% or 90% or 95 to 100%, based on the total amount of nitrogen contained in the propane oxydehydrogenation product gas mixture.

It is of course also possible to separate the nitrogen not by itself from the propane oxydehydrogenation product gas mixture but together with other components of the propane oxydehydrogenation product gas mixture which are possibly undesired in the subsequent reaction stage. For example, the separation line in a separation of the nitrogen from the propane oxydehydrogentation product gas mixture by fractional distillation may be positioned in such a way that, for example, essentially all those components whose boiling point is lower than the boiling point of propene are separated off at the top of the rectification column. These components are primarily the carbon oxides CO and $CO_2$ and unconverted oxygen and ethylene as well as methane. It is of course also possible for only a part of the abovementioned components to be separated off together with the nitrogen.

Depending on the catalyst used for the subsequent catalytic gas-phase oxidation of propene to acrolein and/or acrylic acid, it may furthermore be expedient partially or completely to separate the water contained in the propane oxydehydrogenation product gas mixture from the propane/propene contained in said mixture, in addition to the abovementioned components.

This can be done in a simple manner, for example, by allowing the propane and propene to vaporize with evaporative cooling from the bottom liquid remaining in the separation, by fractional distillation, of those components of the propane oxydehydrogenation product gas mixture which have a lower boiling point than propene, water separating out.

Moreover, the propane oxydehydrogenation product gas mixture depleted in nitrogen and possibly in the abovementioned secondary components and containing propene and unconverted propane can be used directly for the preparation of acrolein and/or acrylic acid by catalytic propene oxidation, as described in the prior art, for example in WO 97/36849 or CN-A 11 05 352. This gas-phase catalytic propene oxidation can of course also be carried out as described in EP-A 117 146, U.S. Pat. Nos. 5,198,578 or 5,183,936. However, it can also be carried out analogously to DE-A 33 13 573, CA-A 12 17 502, U.S. Pat. Nos. 3,161,670 or 4,532,365.

The gas-phase catalytic oxidative conversion of the propene contained in the propane oxydehydrogenation product gas mixture depleted at least in nitrogen (referred to below as residual product gas mixture) to acrolein and/or acrylic acid can be carried out, for example, in one subsequent oxidation stage or in two subsequent oxidation stages. The propane accompanying the propene, and any $N_2$, noble gas, CO, $CO_2$, $H_2O$ and other lower organic compounds present, such as other lower hydrocarbons, act essentially as inert diluent gas. Where acrylic acid is the desired product, as a rule two gas-phase catalytic oxidation stages follow, although one-stage gas-phase catalytic oxidations of propene to acrylic acid are also known from the prior art. If acrolein is the desired product, as a rule only one gas-phase catalytic oxidation stage follows.

The catalytic gas-phase oxidation of the propene contained in the residual product gas mixture to an amount of acrolein which is predominant compared with acrylic acid is preferably carried out as described in EP-A 731 082, DE-A 44 31 957, DE-A 29 09 597 or EP-A 575 897.

In other words, the gas-phase oxidation is effected in an expedient manner in a fixed-bed reactor having multiple catalyst tubes.

As a rule, a volume (1 (S.T.P.)) ratio of propene to oxygen to essentially inert gases of 1:(1.0 to 3.0):(5 to 25), preferably 1:(1.7 to 2.3):(10 to 15), is employed.

To achieve the abovementioned ratios, it may be necessary additionally to introduce molecular oxygen into the propene-containing residual product gas mixture before it is passed into the propene oxidation stage. This can be effected in the form of air, in the form of air depleted in nitrogen or in the form of pure oxygen. Additional diluent gases essentially known to be inert (e.g. $H_2O$) can of course be added as desired at this point. The reaction temperature is expediently chosen to be from 300° C. to 450° C., preferably from 320° C. to 390° C. The reaction pressure is usually from 0.5 to 5, preferably from 1 to 3, bar. The total space velocity is frequently from 1500 to 2500 1 (S.T.P) per 1 per h.

Suitable catalysts for this oxidation stage are, for example, those of DE-A 29 09 592, especially those from Example 1 of this publication. Alternatively, however, the multimetal oxide catalysts II and II' of DE-A 1 97 53 817 may also be used. This applies in particular to the embodiments mentioned by way of example in these publications, especially when they are in the form of unsupported hollow cylinder catalysts as described in EP-A 575 897. Of course, the Bi-, Mo- and Fe-containing multimetal oxide catalyst ACF-2 from Nippon Shokubai can also be used in the propene oxidation stage.

In the abovementioned propene oxidation stage, it is not pure acrolein that is obtained but a mixture from whose secondary components the acrolein can be separated in a manner known per se. The acrolein separated off in this manner can be used as an intermediate for the synthesis of various end products. It can of course also be used for the gas-phase catalytic oxidation for the preparation of acrylic acid. When the acrolein is used for the preparation of acrylic acid in a further gas-phase catalytic oxidation stage, the acrolein-containing reaction gases of the propene oxidation stage are however generally transferred to this further oxidation stage without separation from secondary components. If necessary, they undergo cooling beforehand.

This further oxidation stage is likewise realized in an expedient manner in a fixed-bed reactor having multiple catalyst tubes, as described, for example, in DE-A 44 31 949, DE-A 44 42 346, DE-A 1 97 36 105 or EP-A 731 082.

As a rule, a volume (1 (S.T.P)) ratio of acrolein:oxygen:steam: other essentially inert gases of 1:(1 to 3): (>20): (3 to 30), preferably of 1: (1 to 3): (0.5 to 10): (7 to 18), is used. To achieve the abovementioned ratios, it may be necessary additionally to introduce molecular oxygen into the acrolein-containing product gas mixture from the propene oxidation stage before it is passed into the acrolein oxidation stage. This can be effected in the form of air, in the form of air depleted in nitrogen or in the form of pure oxygen. Of course, additional diluent gases known to be essentially inert may be added at this point as desired. The reaction temperature is expediently chosen to be from 200° C. to 300° C., preferably from 220 to 290° C. The reaction pressure is usually from 0.5 to 5, preferably from 1 to 3, bar. The total space velocity is preferably from 1000 to 2500 1 (S.T.P.) per 1 per h. Suitable catalysts for this oxidation stage are, for example, those of the formula I or I' from DE-A 44 42 346. Alternatively, however, the multimetal oxide catalysts of DE-A 1 97 36 105, in particular the embodiments mentioned in this publication, may also be used. The Bi-, Mo- and Fe-comprising multimetal oxide catalyst ACS-4 from Nippon Shokubai can of course also be used in the acrolein oxidation stage.

Of course, the gas mixture leaving the acrolein oxidation stage does not consist of pure acrylic acid but of a gas mixture which contains the latter and from which acrylic acid can be separated in a manner known per se.

The various known methods for separating off acrylic acid are summarized in, for example, DE-A 1 96 00 955. In a corresponding manner, it could also be possible to separate the acrolein from the reaction gas mixture leaving the propene oxidation stage. A common feature of the separation method is that the desired product is separated from the reaction gas mixture of the acrolein oxidation stage either by absorption with a solvent (cf. also DE-A 43 08 087) or by absorption with water or by partial condensation (the resulting absorbate or condensate is then worked up by distillation (with or without the addition of an azeotropic entraining agent) and/or by crystallization and essentially pure acrylic acid or pure acrolein is thus obtained).

The separation line is drawn essentially in all cases so that a residual gas stream which is essentially free of acrylic acid and/or acrolein and whose main components are carbon oxides (CO, $CO_2$) or possibly $N_2$, noble gases, $O_2$, steam, propane and unconverted propene.

When the novel process is carried out continuously, the propane and propene contained in this residual gas stream are expediently recycled to the oxydehydrogenation. Where the at least partial nitrogen removal required according to the invention after the propane oxydehydrogenation is carried out so that all gas components having a boiling point lower than that of propene are separated off together with the nitrogen, it is expedient to recycle the residual gas stream as such to the propane oxydehydrogenation. By cooling the residual gas stream, however, comparatively readily condensable components, such as steam, small amount of acrylic acid and/or acrolein and small amounts of byproducts, e.g. formaldehyde and acetic acid, can also be separated off in a simple manner (as dilute acid solution) from said residual gas stream before the recycling. Particularly when, according to the invention, only a single, partial or complete nitrogen separation is carried out after the propane oxydehydrogenation, it is advisable, before recycling the residual gas stream to the propane oxydehydrogenation, to separate from said residual gas stream at least a part of the residual gas stream components contained therein and differing from propane and propene. This can be effected in a very simple manner, for example by fractional distillation, in particular fractional distillation under pressure.

EXAMPLES

A) Preparation of acrolein and/or acrylic acid starting from propane a) 15.4 mol/h of a gas mixture (modified air) consisting of 90% by volume of $O_2$ and 10% by volume of $N_2$ and 79.7 mol/h of recycled gas having the composition 87.7% by volume of propane,
0.4% by volume of propene,
4.1% by volume of $O_2$,
2.1% by volume of $N_2$,
2.5% by volume of $H_2O$
0.8% by volume of CO,
1.9% by volume of $CO_2$ and
0.5% by volume of other components, were combined to give 95.1 mol/h of reaction gas starting mixture and compressed to 2.2 bar and heated to 430° C. A 3.8 m long reaction tube of V2A stainless steel (2.0 mm wall thickness, 2.6 cm internal diameter) which was cooled over its total length to 430° C. in a salt bath was fed with the abovementioned reaction gas starting mixture.

In the direction of flow, the reaction tube was loaded first over a length of 0.8 m with spherical (diameter=8 mm) steatite moldings (instead of the steatite beads, steatite rings having the geometry mentioned below and measuring 5 mm×3×2 mm can also be used here). Over the remaining bed length of 3 m, the reaction tube was filled with a bed of the multimetal oxide catalyst according to Example 1, a)/multimetal oxide material I of DE-A 19 753 817, molded to give unsupported catalyst cylinders measuring 5 mm×3 mm×2 mm (external diameter×height×internal diameter). The inlet pressure was 1.3 bar and the outlet pressure 1.0 bar. The product mixture leaving the reaction tube (102.3 mol/h) had the following composition:

59.9% by volume of propane,
6.5% by volume of propene,
4.8% by volume of $O_2$,
3.2% by volume of $N_2$,
16.7% by volume of $H_2O$,
4.3% by volume of CO,
4.0% by volume of $CO_2$,
0.2% by volume of acrolein and
0.4% by volume of other components.

The abovementioned product mixture was compressed at 36 bar, cooled to 70° C. and then fed as a two-phase mixture to a rectification column which was operated under pressure and had 51 trays. The product mixture was fed in at the 30th tray from the bottom. The top pressure of the rectification column (a bubble tray column, diameter 50 mm) was 36 bar.

The top of the column was cooled with the coolant Baysilone® KT3 (feed temperature −50° C.). The bottom temperature was 920° C. At the bottom of the column, a part of the bottom liquid removed was recycled as vapor.

17.4 mol/h of a waste gas which had the following composition:

2.7% by volume of propane,
0.5% by volume of propene,
28.2% by volume of $O_2$,
18.8% by volume of $N_2$,
24.9% by volume of CO
23.2% by volume of $CO_2$ and
1.7% by volume of other components.

were removed at the top of the column.

The continuously removed bottom liquid amounted to 84.9 mol/h. It was cooled at 35° C. and let down to 10 bar into a storage container and brought to 25° C. The gas phase of the storage container was let down to 2.3 bar via a throttle valve. The aqueous liquid phase of the storage container was likewise removed continuously and, after vaporization, was combined with the gas phase which had been removed and let down.

13.6 mol/h of a mixture of 90% by volume of $O_2$ and 10% by volume of $N_2$ and 9.1 mol/h of propane were mixed with the bottom liquid removed and thus continuously transferred to the gas phase, with the result that a reaction starting mixture which had the following composition:

0.2% by volume of acrolein,
65.0% by volume of propane,
6.1% by volume of propene,
11.4% by volume of $O_2$,
1.3% by volume of $N_2$,
15.9% by volume of $H_2O$ and
0.1% by volume of other components formed for the subsequent gas-phase catalytic propene oxidation.

A reaction tube (V2A stainless steel; length 3.80 m; 2.0 mm wall thickness, 2.6 cm internal diameter) was loaded, in the outflow direction, first with an initial bed of steatite beads (diameters: 4–5 mm) over a length of 50 cm. This was followed over a catalyst tube length of 3.00 mm by a bed of the multimetal oxide catalyst according to Example 1,3./ multimetal oxide II from DE-A 19 753 817. The reaction tube was kept at 350° C. over its entire length by means of a salt bath and was fed with 107.6 mol/h of the abovementioned reaction gas starting mixture (which had a temperature of 200° C.).

The inlet pressure was 2.0 bar and the outlet pressure 1.8 bar.

2.4 mol/h of a gas mixture consisting of 90% by volume of $O_2$ and 10% by volume of $N_2$ were mixed with the product gas mixture leaving the reaction tube of the propene oxidation stage, and the acrolein oxidation tube described below was fed with the resulting reaction gas starting mixture, which had been brought to 200° C.

This reaction tube (V2A stainless steel, length 3.80 m, 2,0 mm wall thickness, 2.6 cm internal diameter) was loaded, in the outflow direction, first with an initial bed of steatite beads (diameter 4–5 mm) over a length of 50 cm. This was followed over a catalyst tube length of 2.70 m by a bed of the multimetal oxide catalyst according to Example b, S1 of DE-A 4 442 346. The reaction tube was heated to 270° C. over its entire length by means of a salt bath and was fed with the reaction gas starting mixture described above. The inlet pressure was 1.8 bar and the outlet pressure 1.7 bar. The product mixture leaving the reaction tube in an amount of 107.8 mol/h had the following composition:

0.1% by volume of acrolein, 5.2% by volume of acrylic acid, 0.1% by volume of acetic acid, 64.9% by volume of propane, 0.3% by volume of propene, 3.0% by volume of $O_2$, 1.5% by volume of $N_2$, 22.7% by volume of $H_2O$, 0.6% by volume of CO, 1.4% by volume of $CO_2$ and 0.2% by volume of other components.

The hot reaction gas leaving the acrolein oxidation stage was cooled to about 175° C. in a Venturi scrubber (quench apparatus) by direct contact with quench liquid (140–150° C.) comprising 57.4% by weight of diphenyl ether, 20.7% by weight of biphenyl and 20% by weight o-dimethyl phthalate and sprayed through slots located in the region of the narrowest cross-section of the Venturi tube. In a downstream droplet separator (receiver with gas pipe leading upward), that part of the quench liquid which had remained in the form of liquid drops was then separated from the gas phase consisting of reaction gas and vaporized quench liquid and was recycled in a circulation I to the Venturi scrubber. A part-stream of recycled quench liquid was subjected to a solvent distillation, the quench liquid distilling over and high-boiling secondary components remaining behind and being incinerated. The quench liquid which was distilled over was fed to the discharge of the absorption column described below.

The gas phase which was at about 175° C. was fed to the lower part of a packed absorption column (3 m high, double glass jacket, internal diameter 50 mm, three packing zones having lengths (from bottom to top) of 90 cm, 90 cm and 50 cm, the packing zones were thermostatted from bottom to top as follows: 90° C., 60° C., 20° C., the penultimate and the final packing zone were separated by a chimney tray, the packings were stainless steel helices having a helix diameter of 5 mm and a helix length of 5 mm, the absorbent was fed in immediately above the middle packing zone) and was exposed to the countercurrent of 2400 g/h of the absorbent likewise composed of 57.4% by weight of diphenyl ether, 20.7% by weight of biphenyl and 20% by weight of o-dimethyl phthalate and introduced at 50° C. The discharge of the absorption column, which also contained absorbed low-boiling byproducts, such as acrolein and acetic acid, in addition to acrylic acid, was heated to 100° C. indirectly in a heat exchanger and fed to the top of a desorption column which was likewise in the form of a packed column having a length of 2 m (double glass jacket, 50 mm internal diameter, packings: stainless steel helices having a helix diameter of 5 mm and a helix length of 5 mm, one packing zone having a length of 1 m, thermostatted at 120° C.). In the desorption column, the components having a lower boiling point than acrylic acid, e.g. acrolein and acetic acid, were substantially removed from the acrylic acid/absorbent mixture by stripping with 10 mol/h of recycled gas (countercurrent, feed temperature 120° C.). The laden recycled gas (stripping gas) leaving the desorption column was recirculated and was combined with the hot reaction gas of the acrolein oxidation stage before its entry into the Venturi quench.

The unasborbed gas mixture leaving the second packing zone in an upward direction in the absorption column was further cooled in the third packing zone in order to separate off by condensation the readily condensable part of the secondary components contained therein, e.g. water and acetic acid. This condensate is referred to as dilute acid solution. To increase the separation effect, a part of the dilute acid solution was recycled to the absorption column above the third packing zone of the absorption column at a temperature of 20° C. The dilute acid solution was removed below the uppermost packing zone, from the chimney tray mounted there. The reflux ratio was 200. The continuously removed amount of dilute acid solution was 23.0 mol/h. In addition to 94.3% by weight of water, it also contained 3.0% by weight of acrylic acid. This can, if required, be recovered as described in DE-A 1 96 00 955. The gas stream lastly leaving the absorption column formed the recycle gas which, apart from the portion used in the desorption column for stripping, was recycled to the catalytic propane oxydehydrogenation and had the composition described at the beginning of the example. The amount of recycled gas recycled for the catalytic propane oxydehydrogenation was 79.7 mol/h.

The bottom liquid of the desorption column was fed to the 8th tray from the bottom of a tray column containing 57 dual-flow trays (internal diameter: 50 mm, length 3.8 m, top pressure 100 mbar, bottom pressure 280 mbar, bottom temperature 195° C., a resistance to pressure loss was mounted on the 9th tray) and rectified in said column. 5.4 mol/h of a crude acrylic acid were removed via a side take-off from the 48th tray from the bottom. The purity of the crude acrylic acid removed was ≦98% by weight. After a partial condensation (reflux ratio 8.7), an acrylic acid-containing gas stream enriched in low boilers was taken off at the top of the rectification column and recycled to the absorption column, above the bottom packing zone. The absorbent free of low boilers and virtually free of acrylic acid was taken off from the bottom of the rectification column and recycled to the absorption column, above the second packing zone (considered from the bottom). Phenothiazine as a polymerization inhibitor was added to the reflux at the top of the rectification column, in amounts such that the side take-off contained 300 ppm of phenothiazine (a schematic diagram of the working-up process for the reaction gas of the acrolein oxidation stage is shown in DE-A 1 96 00 955; in addition, the working-up procedure is also described in DE-A 4308087). The yield of acrylic acid was 59.3 mol %, based on the amount of propane used. The oxygen conversion in the oxydehydrogenation stage was 64.7 mol% while the total oxygen conversion was 82.7 mol %.

12.0 mol/h of a gax mixture (modified air) consisting of 90% by volume of $O_2$ and 10% by volume of $N_2$ and 91.6 mol/h of recycled gas having the composition 88.1% by volume of propane, 0.4% by volume of propene, 0.2% by volume of ethene, 3.6% by volume of $O_2$, 2.0% by volume of $N_2$, 2.5% by volume of $H_2O$ 0.8% by volume of CO, 1.9% by volume of $CO_2$ and 0.5% by volume of other components, were combined to give 103.6 mol/h of reaction gas starting mixture, compressed to 1.8 bar and heated to 513° C. An empty reaction tube made of v2A stainless steel (2.0 mm wall thickness, 2,6 cm internal diameter) which was heated to 513° C. over its entire length (electrical heating strip) was loaded with the abovementioned reaction gas starting mixture. The tube length was dimensioned so that the average residence time in the tube was 3 seconds. The product mixture leaving the reaction tube (111.8 mol/h) had the following composition:

63.3% by volume of propane,
6.8% by volume of propene,
1.3% by volume of ethene,
0.5% by volume of methane,
2.0% by volume of $O_2$,
2.8% by volume of $N_2$,
15.8% by volume of $H_2O$
3.3% by volume of CO,
3.7% by volume of $CO_2$ and
0.5% by volume of other components.

The abovementioned product gas mixture was compressed to 36 bar, cooled to 70° C. and then fed as a two-phase mixture to a rectification column which was operated under pressure and had 51 trays. The product mixture was fed in at the 30th tray from the bottom. The top pressure of the rectification column (a bubble tray column, diameter 50 mm) was 36 bar. The top of the column was cooled with Baysilone® KT3 (feed temperature −50° C.). The bottom temperature was 92° C. At the bottom of the column, a part of the bottom liquid removed was recycled as vapor.

16.2 mol/h of a waste gas which had the following composition:

4.0% by volume of propane,
0.8% by volume of propene,
9.0% by volume of ethene,
3.4% by volume of methane,
13.8% by volume of $O_2$,
19.3% by volume of $N_2$,
22.7% by volume of CO,
25.2% by volume of $CO_2$ and
1.8% by volume of other components were thus removed at the top of the column.

The continuously removed bottom liquid amounted to 95.6 mol/h. It was cooled to 35° C. and let down to 10 bar into a storage container and brought to a temperature of 25° C. The gas phase of the storage container was let down to 2.3 bar via a throttle valve. The aqueous liquid phase of the storage container was likewise removed continuously and, after vaporization, was combined with the gas phase which had been removed and let down. 15.0 mol/h of a gas mixture consisting of 90% by volume of $O_2$ and 10% by volume of $N_2$ were mixed with the bottom liquid removed and thus transferred continously into the gas phase, with the result that a reaction gas starting mixture which had the following composition:

63.5% by volume of propane,
6.7% by volume of propene,
12.2% by volume Of $O_2$,
1.4% by volume of $N_2$,
16.0% by volume of $H_2O$,
0.1% by volume of $CO_2$ and
0.1% by volume of other components formed for the subsequent gas-phase catalytic propene oxidation.

A reaction tube (V2A stainless steel, length 3.80 m, 2.0 mm wall thickness, 2.6 cm internal diameter) was loaded, in the outflow direction, first with an initial bed of steatite beads (diameter 4–5 mm) over a length of 50 cm. This was followed over a catalyst tube length of 3.00 m by a bed of the multimetal oxide catalyst according to Example 1,3./multimetal oxide II from DE-A 19 753 817. The reaction tube was heated to 350° C. over its entire length in a salt bath and fed with 110.6 mol/h of the abovementioned reaction gas starting mixture (which had a temperature of 200° C.). The inlet pressure was 1.8 bar and the outlet pressure 1.4 bar.

2.9 mol/h of a gas mixture consisting of 90% by volume of $O_2$ and 10% by volume of $N_2$ were mixed with the product gas mixture leaving the reaction tube of the propene oxidation stage, and the acrolein oxidation tube described below was fed with the resulting reaction gas starting mixture, which had been brought to 200° C. This reaction tube (V2A stainless steel, length 3.80 m, 2.0 mm wall thickness, 2.6 cm internal diameter) was first loaded, in the outflow direction, with an initial bed of steatite beads (diameter 4–5 mm) over a length of 50 cm. This was followed over a catalyst tube length of 2.70 m by a bed of the multimetal oxide catalyst according to Example b, S1 of DE-A 4 442 346. The reaction tube was heated to 270° C. over its entire length by means of a salt bath and was fed with the reaction gas starting mixture described above. The inlet pressure was 1.5 bar and the outlet pressure 1.3 bar. The product mixture leaving the reaction tube in an amount of 110.6 mol/h had the following composition:

0.1% by volume of acrolein,
5.7% by volume of acrylic acid,
0.3% by volume of acetic acid,
62.4% by volume of propane,
0.3% by volume of propene,
0.2% by volume of ethene,
3.0% by volume of $O_2$,
1.7% by volume of $N_2$,
23.5% by volume of $H_2O$,
0.7% by volume of CO,
1.6% by volume of $CO_2$ and
0.5% by volume of other components.

The acrylic acid formed was separated off in a manner corresponding to Aa) from the hot reaction gas leaving the acrolein oxidation stage, and the resulting recycled gas was recycled to the catalytic oxydehydrogenation. Instead of recycled gas, 11.0 mol/h of propane were used for stripping. The laden propane (stripping gas) leaving the desorption column was recirculated and was combined with the hot reaction gas of the acrolein oxidation stage before its entry into the Venturi quench. The amount of dilute acid solution separated off was 24.4 mol/h. It contained 94.3% by weight of water and 3.0% by weight of acrylic acid. The amount of crude acrylic acid separated off in the rectification column via a side take-off was 6.2 mol/h.

Finally, it should be noted that, according to the invention, recycled gas can also be used for stripping instead of propane. In this case, the propane required would be fed directly to the oxydehydrogenation stage.

The yield of acrylic acid was 56.4 mol %, based on the amount of propane used. The oxygen conversion in the oxydehydrogenation stage was 79.4% by volume while the total oxygen conversion was 91.7% by volume.

B) Preparation of 1 mol/s of propene (20° C., 1 bar) by oxydehydrogenation of propane—consideration of the separation work to be performed for nitrogen separation (to simplify the consideration, a complete conversion of the oxydehydrogenation and 100% selectivity of the propene formation will be assumed here).

a) Use of pure $O_2$ as oxygen source

The stoichiometry of the oxydehydrogenation reaction of propane to propene is:

Accordingly, 0.5 mol/s of $O_2$ is required for producing 1 mol/s of propene by oxydehydrogenation of propane.

The starting material for obtaining 0.5 mol/s of $O_2$ is air (78% by volume of $N_2$, 21% by volume of $O_2$ and 1% by volume of remaining gases) whose composition, for the sake of simplicity, is to be assumed to be 80% by volume of $N_2$ and 20% by volume of $O_2$. Furthermore, ideal behavior is to be assumed.

Accordingly, to obtain the 0.5 mol/s of $O_2$, it is possible to start from 2.5 mol/s of air (=mixture of 0.5 mol/s of $O_2$ and 2.0 mol/s of $N_2$) which has a temperature of 20° C. and a pressure of 1 bar.

To separate 0.5 mol/s of pure $O_2$ from the abovementioned 2.5 mol/s of air, the air is cooled to −194° C. while maintaining the pressure of 1 bar and is fed as a boiling liquid to the middle part of a rectification column operated adiabatically at 1 bar, in order to be separated into pure nitrogen via the top and into pure oxygen as a bottom liquid.

To realize this required separation of the mixture, according to K. Sattler, Thermische Trennverfahren, Grundlagen, Auslegung, Apparate, second edition, Verlag Chemie, Weinheim (1995), page 182, a minimum reflux ratio is required at the top of the column when an ideal rectification column, i.e. one having an infinite number of theoretical plates, is used (the greater the required minimum reflux ratio, the greater is the separation work to be performed).

While the reflux ratio at the top of the column in the given separation problem is defined very generally as the ratio of that fraction of the amount of $N_2$ obtained in gaseous form at the top of the rectification column per unit time which is recycled to the rectification column after condensation to that fraction which is removed, the minimum reflux ratio at the top of the column ($v_{min}$) is defined as the ratio of that minimum fraction of the amount of $N_2$ obtained in gaseous form at the top of the rectification column by unit time which must be recycled to the rectification column after condensation to realize the set separation task to that fraction which is removed.

According to the abovementioned citation by K. Sattler, the following is true:

$$v_{min} = \frac{1}{\alpha-1}\left[\frac{X^E}{X^F} - \alpha\frac{1-X^E}{1-X^F}\right]$$

where

α is the relative volatility or separation factor of $N_2$ and $O_2$ (i.e. the ratio of the saturation vapor pressures of $N_2$ and $O_2$ at the mean separation temperature along the rectification column (the separation of the mixture takes place along the total rectification column)).

The boiling point of $N_2$ at 1 bar is −196° C. (=top temperature).

The boiling point of $O_2$ at 1 bar is −183° C. (=bottom temperature).

Thus, the mean boiling point along the rectification column is −190° C. According to VDI Heat Atlas, 5th Edition 1998 (DC6 and DC7), the saturation vapor pressure of $N_2$ at −190° C. is 2.0 bar and the saturation vapor pressure of $O_2$ at −190° C. is 0.48 bar.

The relevant a is thus 2.0:0.48=4.15.

$X^F$ is the molar $N_2$ fraction in the mixture (i.e. in air) fed to the rectification column and to be separated, i.e. $X^F$=0.8 (=80% by volume of $N_2$ in air).

$X^E$ is is the molar $N_2$ fraction in the top take-off. Since pure nitrogen is to be separated off at the top, $X^E$=1.

$v_{min}$ is thus 0.4.

In other words, 0.8 mol/s of $N_2$ must be recycled to the column in order to be able to remove 2 mol/s of pure $N_2$ at the top of the column.

Altogether, 2.8 mol/s of liquid $N_2$ are thus fed to the column per unit time (2.0 mol/s as a component of the liquid air and 0.8 mol/s as reflux at the top of the column), the total amount of which must be vaporized continuously.

To vaporize this amount of liquid, an appropriate amount of liquid must be recycled as vapor to the bottom of the column. At the same time, 0.5 mol/s of $O_2$ must be removed from the bottom of the column.

The oxygen removed in liquid form at the bottom of the column is heated to 20° C. at 1 bar, mixed with 1 mol/s of propane (20° C., 1 bar) and heated to 500° C. while retaining the pressure of 1 bar, and the mixture is subjected to catalytic and/or homogeneous oxydehydrogenation.

The reaction gas mixture consisting of 1 mol/s of propene and 1 mol/s of steam is then cooled to 20° C. while retaining the pressure, the steam condensing completely owing to the large difference in boiling points, and 1 mol/s of pure propene (1 bar, 20° C.) being obtained.

Figure 1:
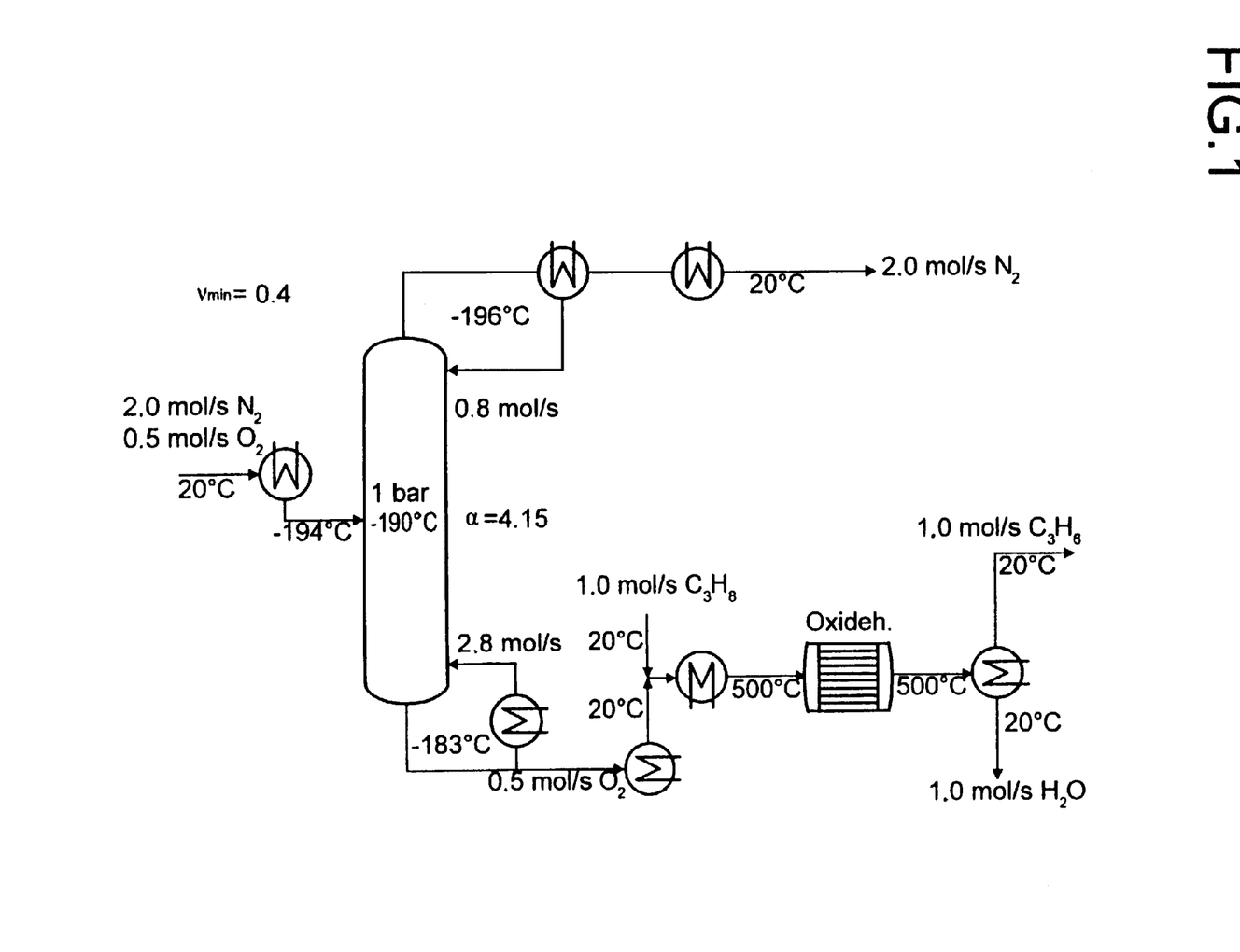
FIG. 1 shows the use of pure oxygen as the oxygen source.

FIG. 1 gives an overview of the above.

b) Use of a mixture of 80% by volume of $O_2$ and 20% by volume of $N_2$.

To obtain the mixture stated in the heading, 2.5 mol/s of air (=mixture of 0.5 mol/s of $O_2$ and 2.0 mol/s of $N_2$) which has a temperature of 20° C. and a pressure of 1 bar are used as a starting material. This is separated in a first rectification column.

The separation by rectification is effected as in a), but into pure nitrogen (top product) and a mixture of 80% by volume of $O_2$ and 20% by volume of $N_2$ (bottom product).

The boiling point of $N_2$ at 1 bar is −196° C. (=top temperature). The boiling point of a mixture of 80% by volume of $O_2$ and 20% by volume of $N_2$ at 1 bar is −187° C. (=bottom temperature).

The mean boiling point along the rectification column is thus −192° C.

According to VDI Heat Atlas, 5th Edition 1998 (DC6 and DC7), the saturation vapor pressure of $N_2$ at −192° C. is 1.62 bar and the saturation vapor pressure of oxygen ($O_2$) is 0,37 bar. The relevant a is thus 1.62:0.37=4.36.

$X^F$ is the molar $N_2$ fraction in the mixture (i.e. in air) fed to the rectification column and to be separated, i.e. $X^F$=0.8 (=80% by volume of $N_2$ in air).

$X^E$ is the molar $N_2$ fraction in the top take-off. Since pure nitrogen is to be separated off at the top, $X^E$=1.

$v_{min}$ is thus 0.37.

In other words, 0.70 mol/s of $N_2$ must be recycled in liquid form to the column in order to be able to remove 1.88 mol/s of pure $N_2$ at the top of the column.

Altogether, 2.7 mol/s of liquid $N_2$ are thus fed to the column per unit time (2.0 mol/s as a component of the liquid air and 0.7 mol/s as a reflux at the top of the column), of which the sum of 1.88 mol/s of $N_2$ (the amount removed at the top) and 0.70 mol/s of $N_2$ (the amount of reflux) must be vaporized per unit time.

In order to vaporize this amount of liquid, a corresponding amount of liquid must be recycled in vapor form to the bottom of the column. At the same time, a mixture of 0.5 mol/s of $O_2$ (80% by volume) and 0.12 mol/s of $N_2$ (20% by volume) must be removed continuously from the bottom of the column.

The mixture of 0.50 mol/s Of $O_2$ and 0.12 mol/s of $N_2$ thus obtained is heated to 20° C. while maintaining the pressure of 1 bar and is mixed with 1.0 mol/s of propane which likewise has a pressure of 1 bar. The mixture is heated to 500° C. while maintaining the pressure and is subjected to catalytic and/or homogeneous oxydehydrogenation under these conditions (complete conversion, ideal selectivity).

The resulting reaction product mixture is cooled to 20° C. while maintaining a pressure of 1 bar, the water of reaction completely condensing owing to the large difference in boiling points. The remaining mixture which is at 20° C. and 1 bar comprises 0.12 mol/s of $N_2$ and 1 mol/s of propene is cooled (−171° C.), while maintaining the pressure, until it can be fed as a boiling liquid into the middle part of a second rectification column (infinite number of theoretical plates) operated adiabatically at 1 bar, in order to be separated into pure nitrogen via the top and into pure propene as a bottom liquid.

The boiling point of $N_2$ at 1 bar is −196° C. (=top temperature).

The boiling point of propene at 1 bar is −48° C. (=bottom temperature).

The mean boiling point along the rectification column is thus −122° C.

According to VDI Heat Atlas, 5th Edition 1998 (DC6 and DC7), the saturation vapor pressure of $N_2$ at −122° C. is 94.8 bar and the saturation vapor pressure of propene at −122° C. is 0.00476 bar. The a relevant in the second rectification column is thus 94.8:0.00476=19900.

$X^F$ is the molar $N_2$ fraction in the mixture fed to the rectification column and to be separated.

In other words, $X^F$=0.12/1.12=0.107. $X^E$ is the molar $N_2$ fraction in the top take-off. Since pure nitrogen is to be taken off at the top, $X^E$=1.

$v_{min}$ is thus 0.00047.

In other words, 0.000056 mol/s of $N_2$ must be recycled in liquid form to the column in order to be able to remove 0.12 mol/s of $N_2$ at the top of the column.

Altogether, 0.120056 mol/s of liquid $N_2$ is thus fed to the column per unit time (0.12 mol/s as a component of the liquid mixture fed in and 0.000056 mol/s at the top of the column), the total amount of which must be vaporized continuously.

In order to vaporize this amount of liquid, a corresponding amount of liquid must be recycled in vapor form to the bottom of the column. At the same time, 1.0 mol/s of propene is removed from the bottom of the column and heated to 20° C. while maintaining the pressure (1 bar).

Figure 2:
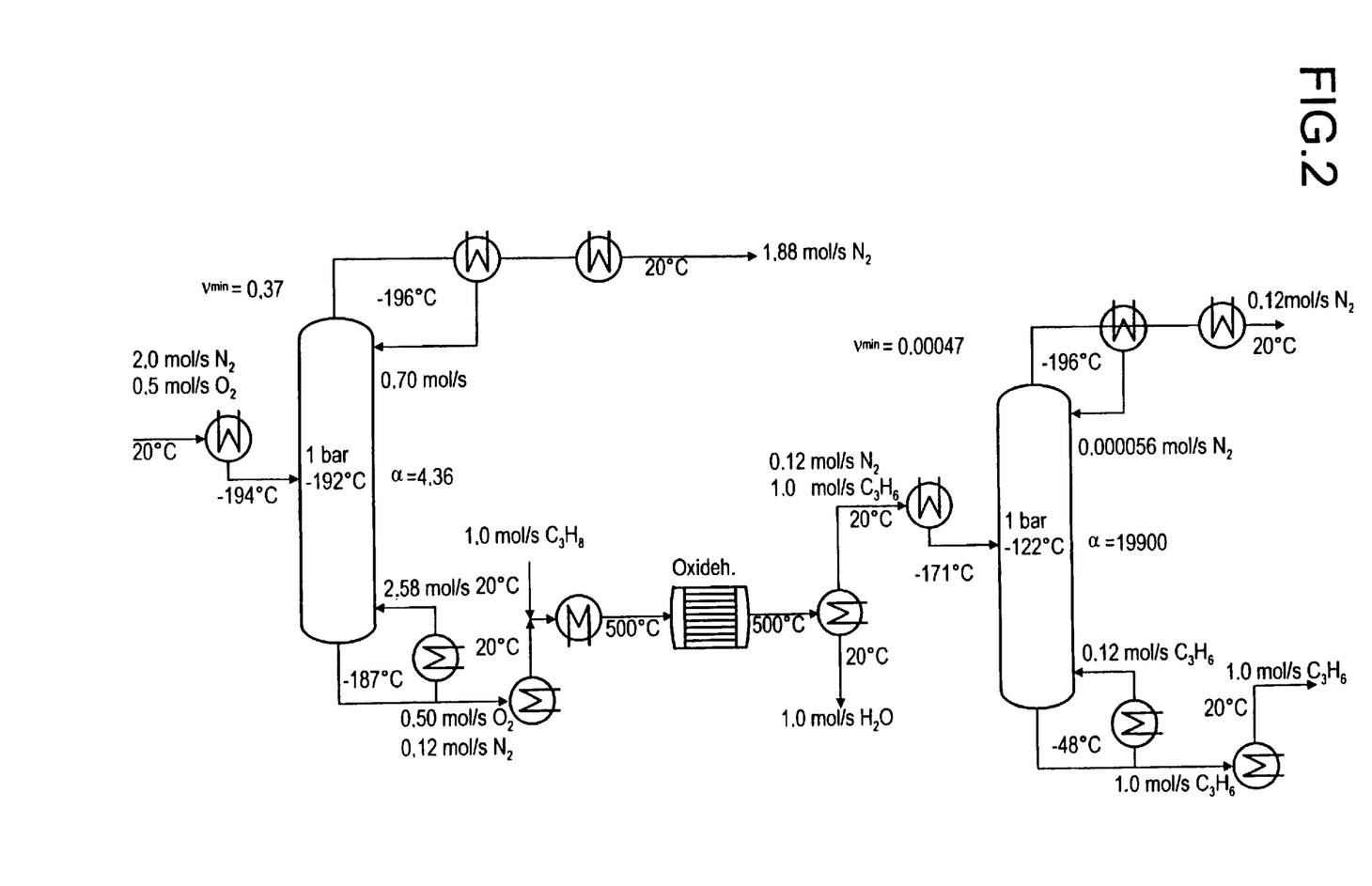
FIG. 2 shows the use of a mixture of 80% by volume of oxygen and 20% by volume of nitrogen.

FIG. 2 gives an overview of the above.

If routes a) and b) are compared with one another, the lower $v_{min}$ in case ($\Sigma v_{min}$=0.37+0.00047=0.3705) in contrast to $v_{min}$=0.4 in case a) shows that less separation work has to be performed when air only partially depleted with respect to nitrogen is used.

We claim:

1. A process for the preparation of acrolein, acrylic acid from propane, in which the propane is subjected, in a first reaction stage, to a partial oxydehydrogenation with molecular oxygen under homogeneous catalysis, heterogeneous catalysis or the combination of homogeneous and heterogeneous catalysis to give propene and the propene-containing product gas mixture formed in the first reaction stage is then used in at least one further reaction stage for the preparation of acrolein and/or acrylic acid by gas-phase catalytic propene oxidation, wherein the molecular oxygen required in the first reaction stage and differing from recycled oxygen gas is added as nitrogen-containing modified air to the reaction gas starting mixture of the first reaction stage, with the proviso that the nitrogen content of the modified air is less than, and the oxygen content of the modified air is greater than, the corresponding contents of air, and wherein at least a part of the molecular nitrogen contained in the product gas mixture is separated from said mixture before the further use of propene-containing product gas mixture, formed in the first reaction stage, for the preparation of acrolein, acrylic acid in the at least one further reaction stage.

2. A process as claimed in claim 1, wherein the total amount of the nitrogen contained in the product gas mixture is separated off before the further use of propene-containing product gas mixture, formed in the first reaction stage, for the preparation of acrolein, acrylic acid in the at least one further reaction stage.

3. A process as claimed in claim 1, wherein the nitrogen is separated off by fractional distillation.

4. A process as claimed in claim 3, wherein with the separation of the nitrogen, a separation of all components of the product gas mixture which have a boiling point lower than that of propene is carried out.

5. A process as claimed in claim 2, wherein the nitrogen is separated off by fractional distillation.

6. A process as claimed in claim 2, wherein, with the separation of the nitrogen, a separation of all components of the product gas mixture which have a boiling point lower than that of propene is carried out.

7. A process as claimed in claim 5, wherein, with the separation of the nitrogen, a separation of all components of the product gas mixture which have a boiling point lower than that of propene is carried out.

\* \* \* \* \*